United States Patent
Kang et al.

(10) Patent No.: US 7,067,233 B2
(45) Date of Patent: Jun. 27, 2006

(54) COMPOUND HAVING AN EPOXY GROUP AND A CHALCONE GROUP, METHOD OF PREPARING THE SAME, AND PHOTORESIST COMPOSITION COMPRISING THE SAME

(75) Inventors: Yoon-Ho Kang, Yongin-si (KR); Dong-Ho Bae, Suwon-si (KR); Jang-Sub Kim, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 6 days.

(21) Appl. No.: 10/807,861

(22) Filed: Mar. 24, 2004

(65) Prior Publication Data
US 2005/0089793 A1    Apr. 28, 2005

(30) Foreign Application Priority Data
Oct. 27, 2003   (KR) .................. 10-2003-0075086

(51) Int. Cl.
*G03F 7/028* (2006.01)
*G03F 7/029* (2006.01)

(52) U.S. Cl. .................. 430/280.1; 528/90; 528/95; 528/98; 549/517

(58) Field of Classification Search ............ 430/280.1; 528/90, 95, 98; 549/517
See application file for complete search history.

(56) References Cited
U.S. PATENT DOCUMENTS
3,295,974 A * 1/1967 Erdmann .................. 430/280.1
(Continued)

FOREIGN PATENT DOCUMENTS
DE          2 256 961    * 5/1974

OTHER PUBLICATIONS
Panda, S. P., Journal of Polymer Science: Polymer Chemistry Edition, vol. 13, 1975, pp. 1757-1764.*
(Continued)

Primary Examiner—Cynthia Hamilton
(74) Attorney, Agent, or Firm—F. Chau & Associates, LLC

(57) ABSTRACT

A compound including an epoxy group that has a heat curing property and a chalcone group that has a radiation curing property is represented by the following formula:

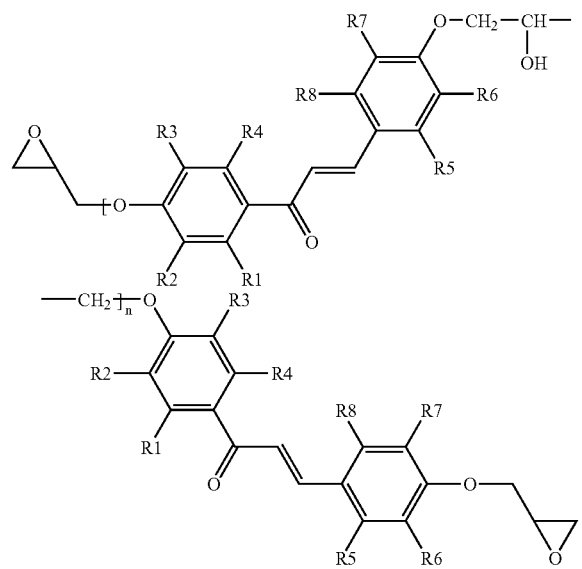

wherein n is an integer from 1 to 10,000, and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group. The compound has a high curing efficiency. A photoresist composition including the compound above substantially prevents the formation of remnant in a photoresist pattern used in the manufacturing of a color filter. In addition, the color filter pattern that is formed using the photoresist composition has high color reproductivity and brightness.

11 Claims, 9 Drawing Sheets

U.S. PATENT DOCUMENTS 3,410,824 A * 11/1968 Atkinson .................... 528/95
2003/0017351 A1 * 1/2003 Hayashi et al. .......... 428/473.5

OTHER PUBLICATIONS

Zahir, Journal of Applied Polymer Science, John Whiley & Sons, 1979, vol. 23, pp. 1355-1372.*

Choi et al, European Polymer Journal, vol. 37, Issue 10, Oct. 2001, pp. 1951-1959, available on line Jul. 25, 2001 at Science Direct.com.*

Choi et al , Bull. Korean Chem. Soc. 2001, vol. 22, No. 11, pp. 1207-1212.*

Knoval Critical Tables, Table Enthalpy & Entropy of Formation of Organic Compounds in Condensed Phase Row (RecordO No.:1734, 1,3-diphenyl-2-propene-1-one, from http://www.knovel.com.*

Knoval Critical Tables, Table Enthalpy & Entropy of Formation of Organic Compounds in Condensed Phase Row (RecordO No.: 9675, epichorohydrin, from http://www.knovel.com.*

Choi et al, Polymer, vol. 43, (Feb. 2002), pp. 703-710 available online Nov. 26, 2001 at www.sciencedirect.com.*

An 82:73919 CA, English abstract of DE 2256961, issued May 1974, 2 pages, Chemical Abstracts.*

76:127888 CA, English abstract of Panda, Indian Journal of Technology (1971), 9 (10), 387-90.*

81:26365 CA, English abstract of Panda and several registry number sheets cited therein attached, Indian Journal of Technology ((1973), 11 (8), 356-9.*

* cited by examiner

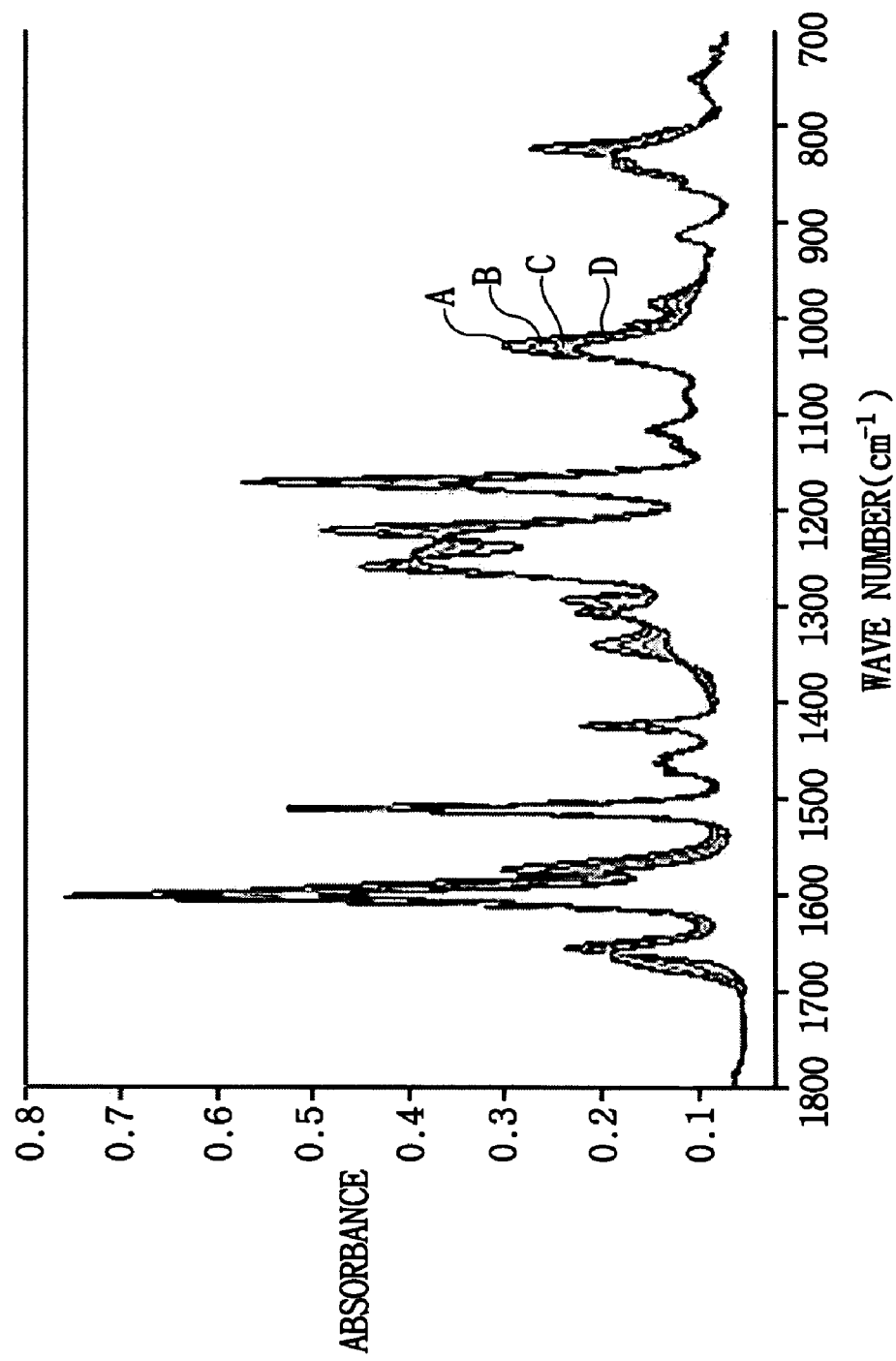

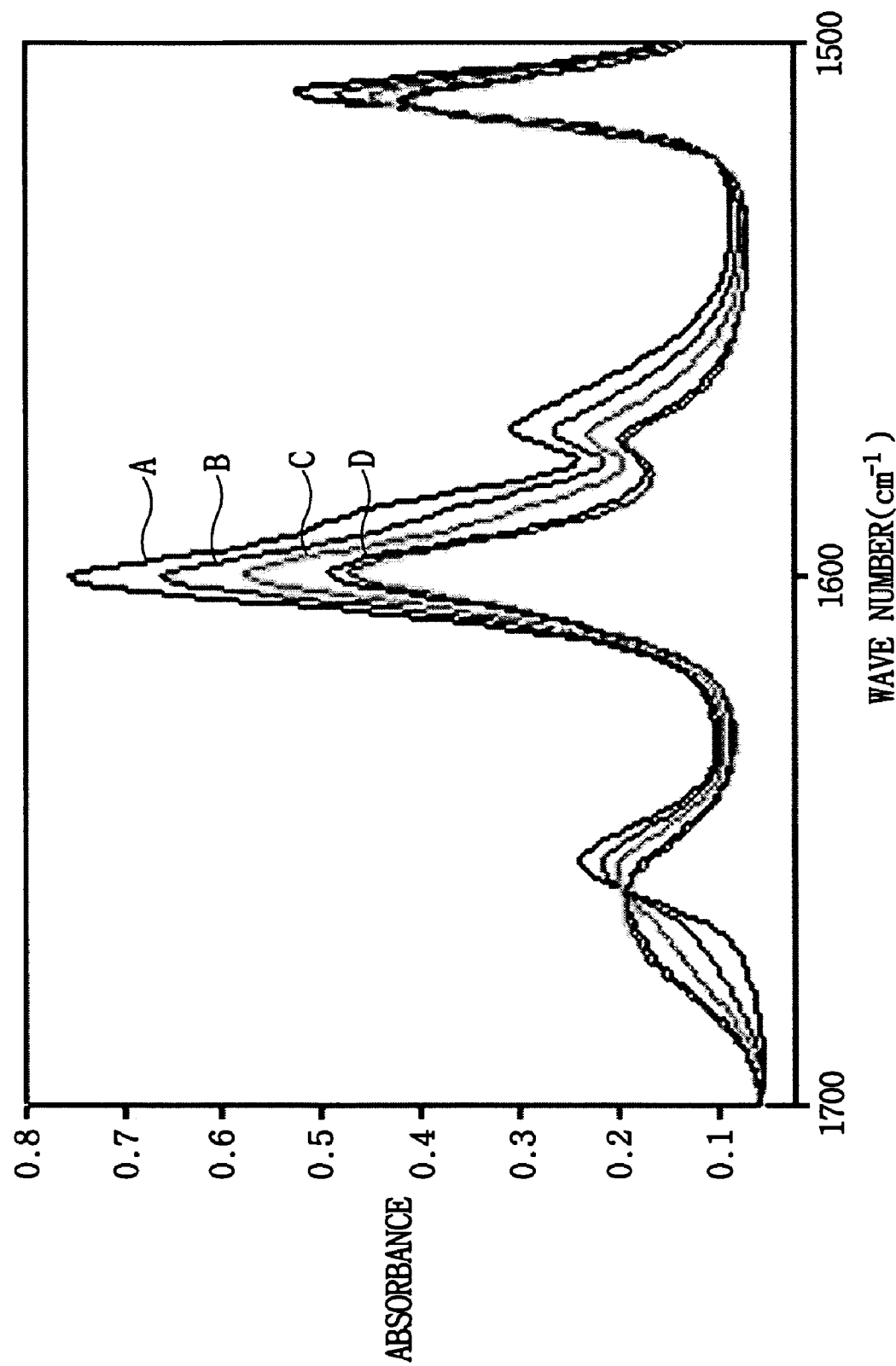

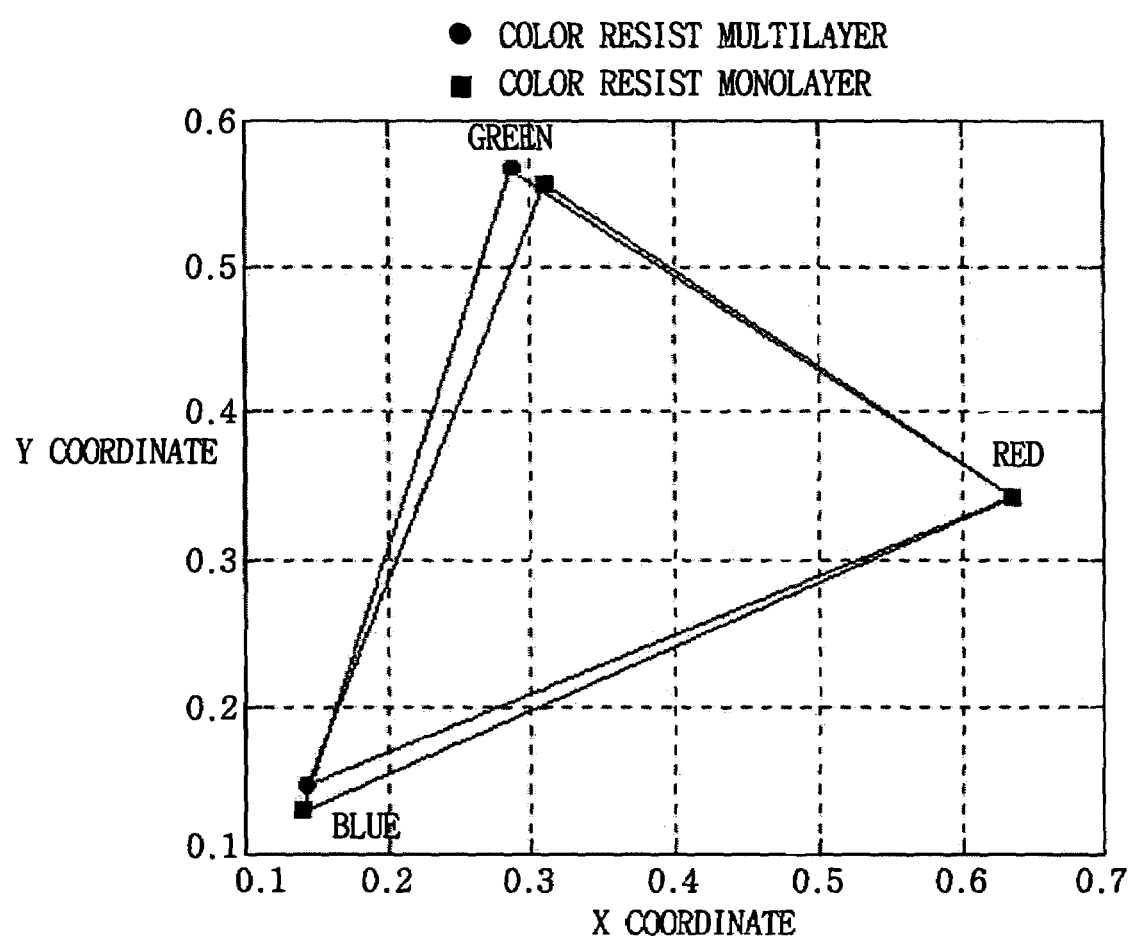

COMPOUND HAVING AN EPOXY GROUP AND A CHALCONE GROUP, METHOD OF PREPARING THE SAME, AND PHOTORESIST COMPOSITION COMPRISING THE SAME

CROSS-REFERENCE TO RELATED APPLICANTIONS

This application claims priority from Korean Patent Application No. 2003-75086 filed on Oct. 27, 2003, which is incorporated by reference in its entirety.

BACKGROUND OF THE INVENTION

1. Technical Field

The present invention relates, generally, to a compound having an epoxy group and a chalcone group, a method of preparing the same, and a photoresist composition comprising the same. More particularly, the present invention relates to a compound having an epoxy group that has a heat curing property and a chalcone group that has a radiation curing property, a method of preparing the same, and a photoresist composition comprising the same.

2. Discussion of the Related Art

Liquid crystal display apparatuses (LCDs) are widely used in various devices, such as cellular phones, billboards, computer monitors, televisions, etc., because of the many advantages LCDs provide. These advantages include much lower power consumption than other display devices and being thinner and lighter than cathode ray tubes.

Generally, to display an image, an LCD apparatus includes an LCD panel and a backlight assembly for supplying light to the LCD panel. The LCD panel includes liquid crystal interposed between two glass substrates. Transmittance of light through the LCD panel is adjusted by controlling and varying the voltage applied to the pixels of the LCD panel.

To display color, an LCD apparatus can use three sub-pixels with color filters, e.g., a red filter, a green filter and a blue filter, to create each color pixel. The transmitted light that passes through the color filters is additively mixed to display a full color screen. For high color reproductivity and brightness close to natural color, the liquid crystal display apparatus needs to have high resolution and light efficiency, and the color filter must be precisely patterned.

Photoresist compositions are used for patterning color filters. A conventional photoresist composition includes an acrylate resin, a curing agent and an organic solvent. The photoresist composition may further include a pigment when used for manufacturing a color filter. The acrylate resin has a radiation curing property. The acrylate resin provides a photo cross-linking reaction during an exposure process and then acts as a binder between a pattern and the pigment.

In the conventional photoresist compositions, the acrylate resin is usually not completely cured. Hence, a molecular interaction occurs between the surface of a photoresist pattern and a subsequently applied photoresist composition or dispersant for the pigment, thereby generating a photoresist composition remnant. The remnant deteriorates the color characteristics and reduces brightness of the color filter. Moreover, the remnant may cause failures in a junction to a pixel electrode. In particular, when a photoresist multilayer pattern is formed, a color coordinate may be moved, thereby reducing the brightness of the color filter.

Therefore, a need exists for a photoresist composition that prevents the formation of a remnant in a photoresist pattern used in forming a color filter to provide a color filter having improved color reproductivity and brightness.

SUMMARY OF THE INVENTION

It is a feature of the present invention to provide a compound having an epoxy group that has a heat curing property and a chalcone group that has a radiation curing property.

It is another feature of the present invention to provide a method of preparing the compound.

It is still another feature of the present invention to provide a photoresist composition including the composition.

Exemplary Embodiments of the present invention are directed toward a composition comprising an epoxy group and a chalcone group. The compound comprising an epoxy group and a chalcone group is represented by the following formula:

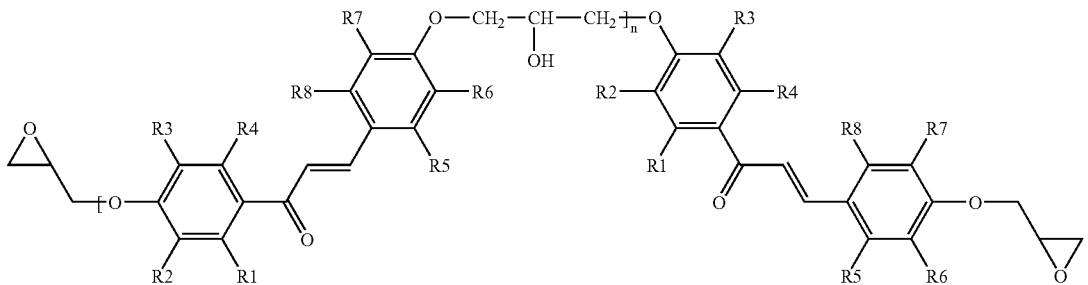

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group.

In addition, the compound has a weight average molecular weight of about 800 to about 20,000.

According to another exemplary embodiment, a process for preparing a compound including an epoxy group and a chalcone group is provided. The process comprises reacting bis(4-4'-hydroxy)chalcone with epichorohydrin in the presence of an alkali metal salt to synthesize a compound represented by the following formula:

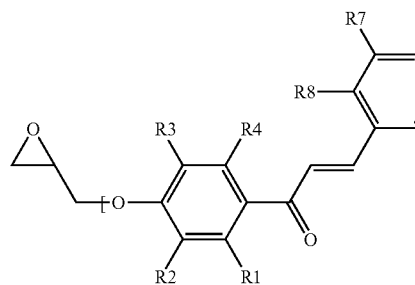

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group.

The process may also include reacting bis[4,4'-(2-2'-tetrahydro-2H-pyranoxy)]chalcone with a paratoluene sulfonic acid in the presence of an alcohol to synthesize the bis(4-4'-hydroxy)chalcone.

In addition, the process may include reacting 4-(2-tetrahydro-2H-pyranoxy)acetohenone with 4-(2-tetrahydro-2H-pyranoxy)benzaldehyde in the presence of an alkali metal salt to synthesize the bis[4,4'-(2-2'-tetrahydro-2H-pyranoxy)]chalcone.

Further, the process may include reacting 4-hydroxy benzaldehyde with 3,4 dihydro-2H-pyran to synthesize the 4-(2-tetrahydro-2H-pyranoxy)benzaldehyde.

Furthermore, the process may include reacting 4-hydroxy acetophenone with 3,4 dihydro-2H-pyran to synthesize the 4-(2-tetrahydro-2H-pyranoxy)acetohenone.

According to yet another exemplary embodiment, a resist composition including a compound having an epoxy group and a chalcone group is provided. The resist composition comprising a curing agent, an organic solvent, and a compound comprising an epoxy group and a chalcone group represented by the following formula:

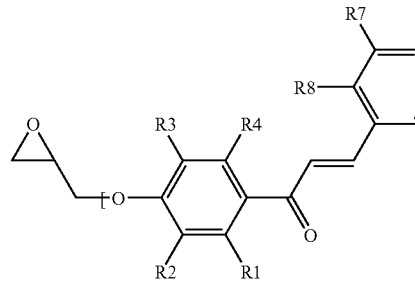

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group;

In addition, the resist composition may include about 5 to about 35 parts by weight of the compound, about 0.01 to about 5 parts by weight of the curing agent, and 60 to about 90 by weight of the organic solvent.

Further, the resist composition may include an acrylate resin. The resist composition may also include about 5 to

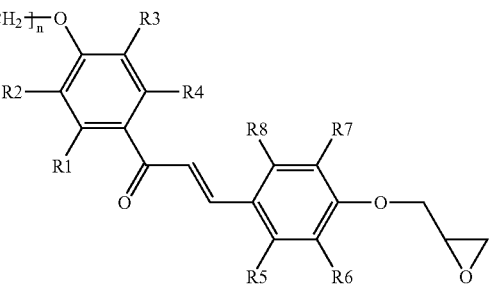

about 35 parts by weight of a combination of the acrylate resin and the compound, about 0.01 to about 5 parts by weight of the curing agent, and about 60 to about 90 by weight of the organic solvent.

According to still yet another exemplary embodiment, a method for forming a color resist pattern is provided. The method for forming a color resist pattern comprising the steps of applying a layer of a first color resist composition to a black matrix on a substrate to form a first color resist layer, wherein the first color resist composition includes a compound having a chalcone and an epoxy group, a curing agent, an organic solvent, and a pigment, baking the first color resist layer, wherein the organic solvent is evaporated, disposing a first mask having patterns over the first color resist layer, exposing a portion of the first color resist layer through the first mask, developing the exposed first color resist layer, wherein the exposed portion of the first color resist is dissolved in a developing solution, and heating the substrate with the developed first color resist layer, thereby forming a first color resist pattern.

These and other exemplary embodiments, features, aspects, and advantages of the present invention will be described in more detail and become more apparent from the following detailed description of exemplary embodiments with reference to the accompanying drawings.

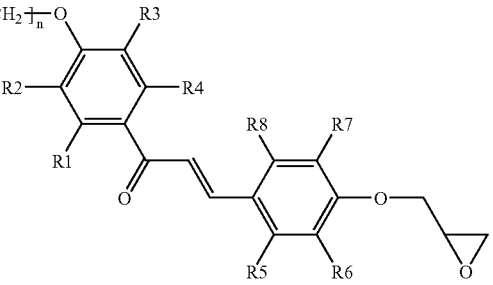

BRIEF DESCRIPTION OF THE DRAWINGS

FIG. 3A represents infrared spectra of the compound obtained in Example 1 with respect to time.

FIG. 3B represents enlarged infrared spectra of FIG. 3A having a wave number of 1500 to 1700 $cm^{-1}$.

FIG. 4 is a graph illustrating color characteristics of a monolayer and multilayer using a conventional photoresist composition of Comparative Example 1.

DETAILED DESCRIPTION OF EXEMPLARY EMBODIMENTS

Figure 1A:
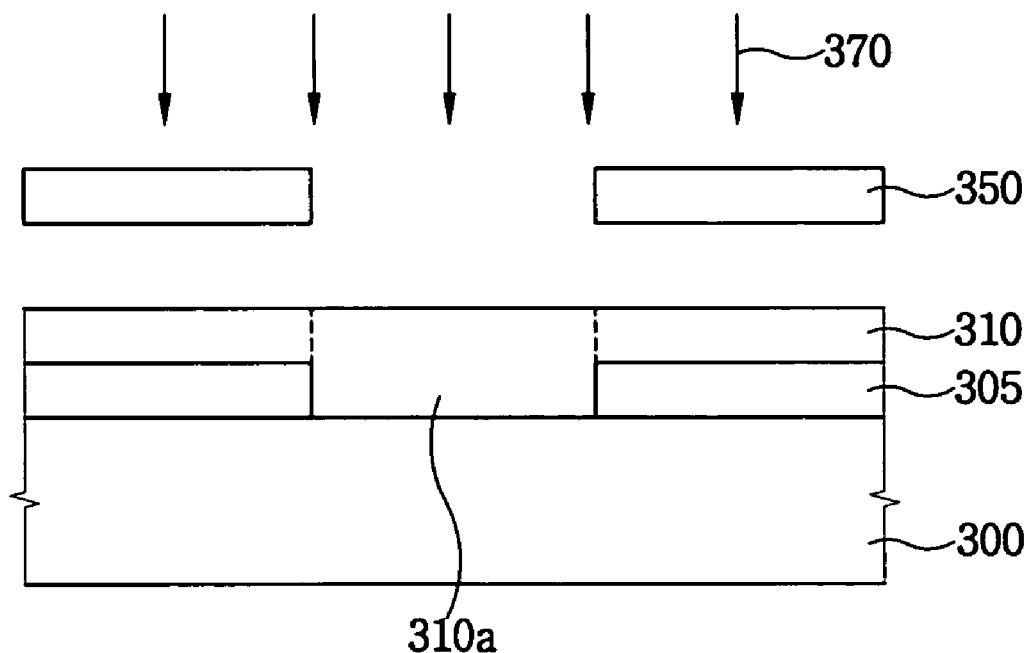
FIGS. 1A and 1B are cross-sectional views illustrating a formation of a color resist pattern using a compound according to an exemplary embodiment of the present invention.

Hereinafter the exemplary embodiments of the present invention will be described in detail with reference to the accompanying drawings.

Compound Having an Epoxy Group and a Chalcone Group

A compound according to the present invention comprising an epoxy group and a chalcone group is represented by the following formula (I).

When the weight average molecular weight of the compound is more than 20,000, the viscosity of the compound increases. When the weight average molecular weight of the composition is less than 800, the compound is excessively used in a photoresist composition, which is not preferable.

In formula (I), the integer n represents a repeat unit of a polymer. As the integer n increases, the compound has more chalcone groups than epoxy groups, thereby imparting the characteristic, radiation curing property, of the chalcone group to the compound. The radiation curing property of the chalcone group is caused by the molecular activation of double bonds in a main chain. In addition, after a curing process, the chalcone group becomes harder because the chalcone group has a benzene ring.

Substituents in the compound represent additional characteristics of the compound other than the characteristics from the main chain. For instance, when comparing solubility in a nonpolar organic solvent of the compounds with and without substitutents, the solubility increases if each of the substituents $R_1$, $R_2$, $R_3$, $R_4$, $R_5$, $R_6$, $R_7$ and $R_8$ is an alkyl

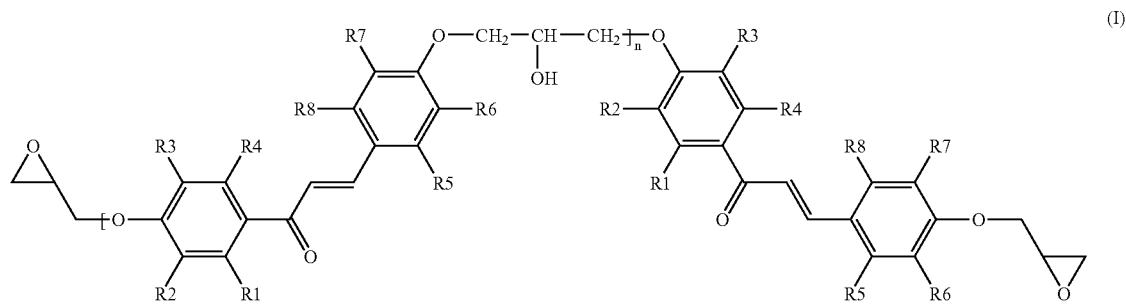

(I)

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group.

The epoxy group of compound I has a heat curing property and the chalcone group of compound I has a radiation curing property.

The compound has a weight average molecular weight of about 800 to about 20,000. The weight average molecular weight of the compound can be determined using a gel permission chromatography (GPC).

group, alkoxy group or halogen atom, and the solubility decreases if each of the substituents $R_1$, $R_2$, $R_3$, $R_4$, $R_5$, $R_6$, $R_7$ and $R_8$ is a nitro group, based on the solubility when each of the substituents $R_1$, $R_2$, $R_3$, $R_4$, $R_5$, $R_6$, $R_7$ and $R_8$ is a hydrogen atom.

Method of Preparing a Compound Having the Epoxy Group and the Chalcone Group

The compound of formula (I) is produced by polymerizing bis(4,4'-hydroxy)chalcones of formula (II) with epichlorohydrin:

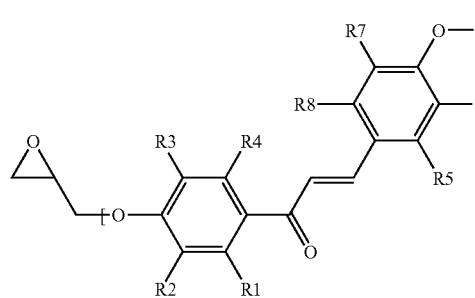

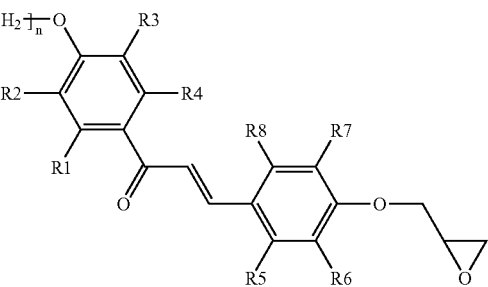

(I)

(II)

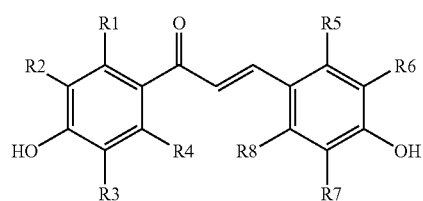

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group.

The polymerization reaction is carried out in the presence of an alkali metal salt. Examples of the alkali metal salt include sodium hydroxide, potassium hydroxide, etc.

The mechanism of the above reaction is as follows:

wherein n, $R_1$, $R_2$, $R_3$, $R_4$, $R_5$, $R_6$, $R_7$ and $R_8$ are as described above.

In particular, two end hydroxyl groups in bis(4,4'-hydroxy)chalcones of formula (II) react with epichlorohydrin. Thus, epoxy groups are formed at both ends of bis(4,4'-hydroxy)chalcones. The epoxy rings formed at the ends of the bis(4,4'-hydroxy)chalcones are opened in the presence of an alkali metal salt, and then the open epoxy rings of a

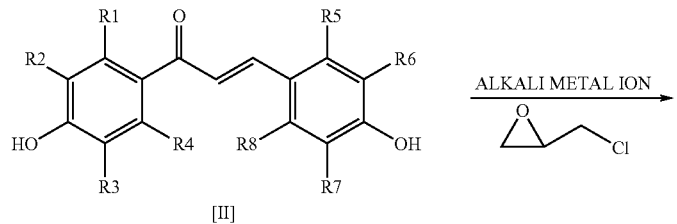

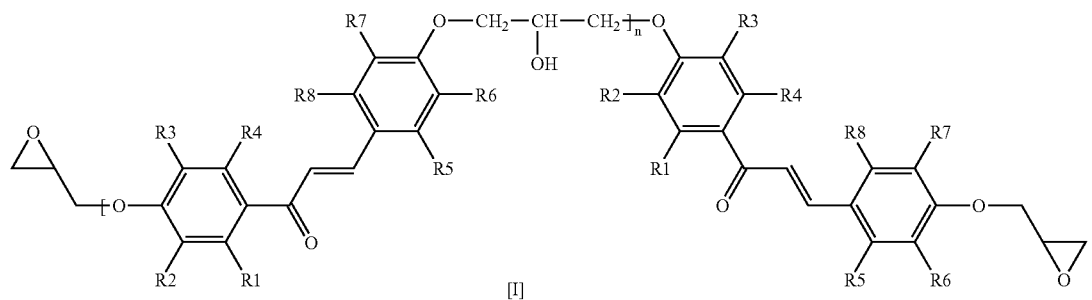

bis(4,4'-hydroxy)chalcone react with other open epoxy rings of another bis(4,4'-hydroxy)chalcone to form a polymer resin compound of formula (I).

After the reaction is completed, a compound having epoxy groups at both ends and a chalcone group inside the main chain is obtained.

Bis(4,4'-hydroxy)chalcones of formula (II) are prepared by reacting bis[4,4'-(2,2'-tetrahydro-2H-pyranoxy)]chalcones of formula (III) with paratoluene sulfonic acid:

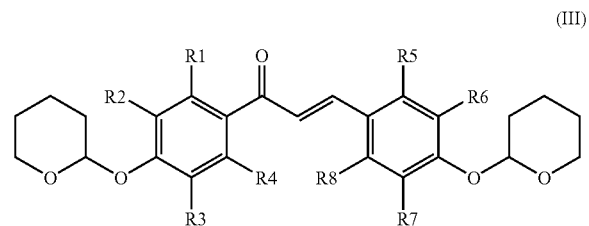

wherein each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group.

The reaction is carried out in the presence of an alcohol. Examples of the alcohol include ethanol, etc.

The mechanism of the above reaction is as follows:

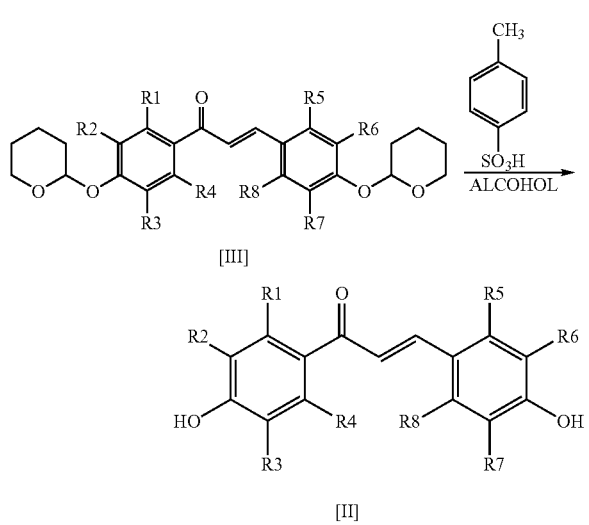

wherein $R_1$, $R_2$, $R_3$, $R_4$, $R_5$, $R_6$, $R_7$ and $R_8$ are as described above.

In particular, when bis[4,4'-(2,2'-tetrahydro-2H-pyranoxy)]chalcones react with paratoluene sulfonic acid, tetrahydropyran at both ends of the bis[4,4'-(2,2'-tetrahydro-2H-pyranoxy)]chalcones are removed. Then, hydrogen atoms in ethanol bond to the positions where tetrahydropyran has been removed to form bis(4,4'-hydroxy)chalcones of formula (II).

Bis[4,4'-(2,2'-tetrahydro-2H-pyranoxy)]chalcones of formula (III) are prepared by reacting 4-(2-tetrahydro-2H-pyranoxy)acetophenones of formula (IV) with 4-(2-tetrahydro-2H-pyranoxy)benzaldehydes of formula (V):

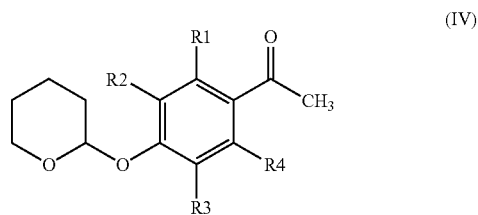

wherein each of $R_1$, $R_2$, $R_3$ and $R_4$ is selected from a group consisting of a hydrogen atom, alkyl group, alkoxy group, halogen atom and nitro group,

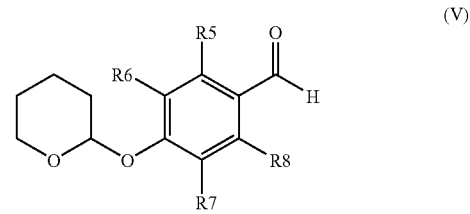

wherein each of $R_5$, $R_6$, $R_7$ and $R_8$ is selected from a group consisting of a hydrogen atom, alkyl group, alkoxy group, halogen atom and nitro group.

The reaction is carried out in the presence of an alkali metal salt. Examples of the alkali metal salt include sodium hydroxide, potassium hydroxide, etc.

The mechanism of the above reaction is as follows:

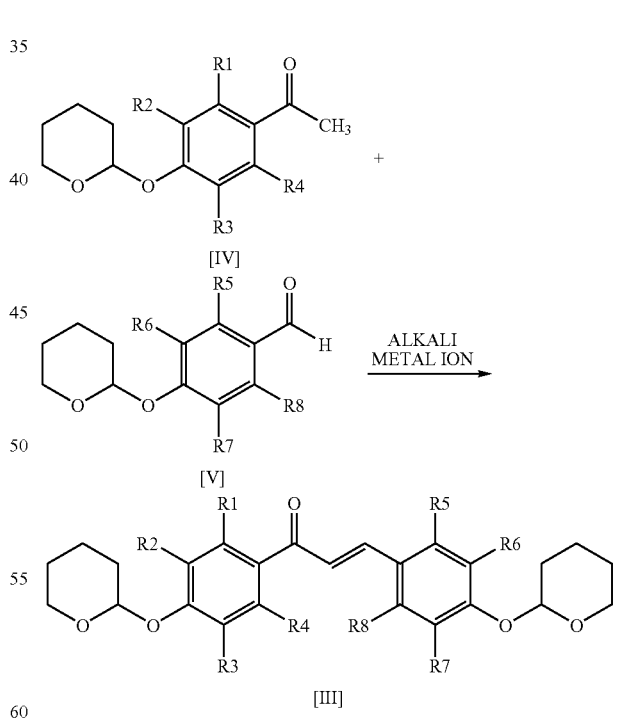

wherein $R_1$, $R_2$, $R_3$, $R_4$, $R_5$, $R_6$, $R_7$ and $R_8$ are as described above.

In particular, 4-(2-tetrahydro-2H-pyranoxy)acetophenones of formula (IV) react with 4-(2-tetrahydro-2H-pyranoxy)benzaldehydes of formula (V) in the presence of an alkali metal salt. A condensation reaction between a ketone group and aldehyde group is carried out to form a bis[4,4'-(2,2'-tetrahydro-2H-pyranoxy)]chalcone of formula (III) that has a central enone group. The functional group that has an enone group and a phenyl group at both ends is referred to as a chalcone group.

4-(2-tetrahydro-2H-pyranoxy)acetophenones of formula (IV) are prepared by reacting 4-hydroxy acetophenones of formula (VI) with 3,4-dihydro-2H-pyran:

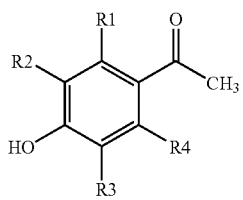
(VI)

wherein each of $R_1$, $R_2$, $R_3$ and $R_4$ is selected from a group consisting of a hydrogen atom, alkyl group, alkoxy group, halogen atom and nitro group.

The mechanism of the above reaction is as follows:

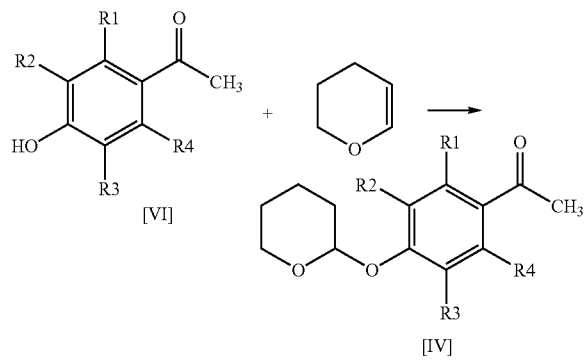

wherein $R_1$, $R_2$, $R_3$ and $R_4$ are as described above.

In particular, 4-hydroxy acetophenones of formula (VI) react with 3,4-dihydro-2H-pyran to give 4-(2-tetrahydro-2H-pyranoxy)acetophenones of formula (IV). A carbon-carbon double bond in 3,4-dihydro-2H-pyran reacts with a hydroxyl group of 4-hydroxy acetophenones of formula (VI) to connect 3,4-dihydro-2H-pyran to 4-hydroxy acetophenones through an oxygen atom.

4-(2-tetrahydro-2H-pyranoxy)benzaldehydes of formula (V) are generated from the reaction of 4-hydroxy benzaldehyde of formula (VII) with 3,4-dihydro-2H-pyran:

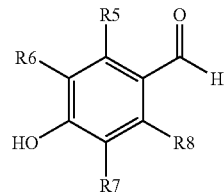
(VII)

wherein each of $R_5$, $R_6$, $R_7$ and $R_8$ is selected from a group consisting of a hydrogen atom, alkyl group, alkoxy group, halogen atom and nitro group.

The mechanism of the above reaction is as follows:

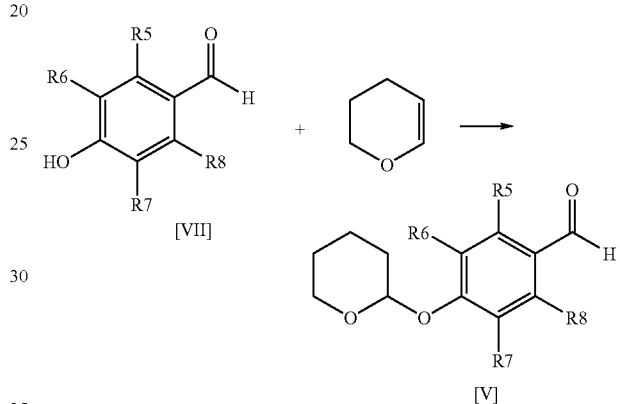

wherein $R_5$, $R_6$, $R_7$ and $R_8$ are as described above.

4-hydroxy benzaldehydes of formula (VII) undergo the same reaction mechanism as described above with respect 3,4-dihydro-2H-pyran reacting with 4-hydroxy acetophenones of formula (VI) except that 4-(2-tetrahydro-2H-pyranoxy)benzaldehydes of formula (V) are formed.

A total reaction scheme of the reactions is as follows:

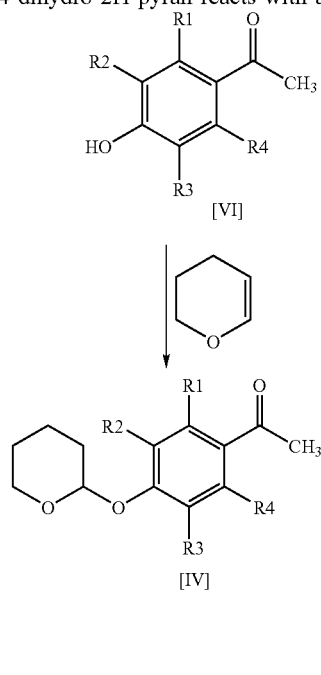
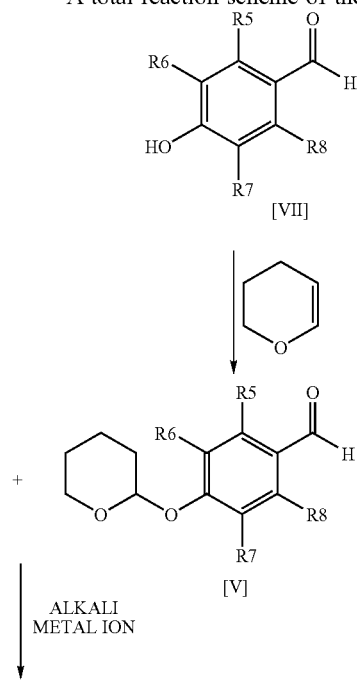

ALKALI METAL ION

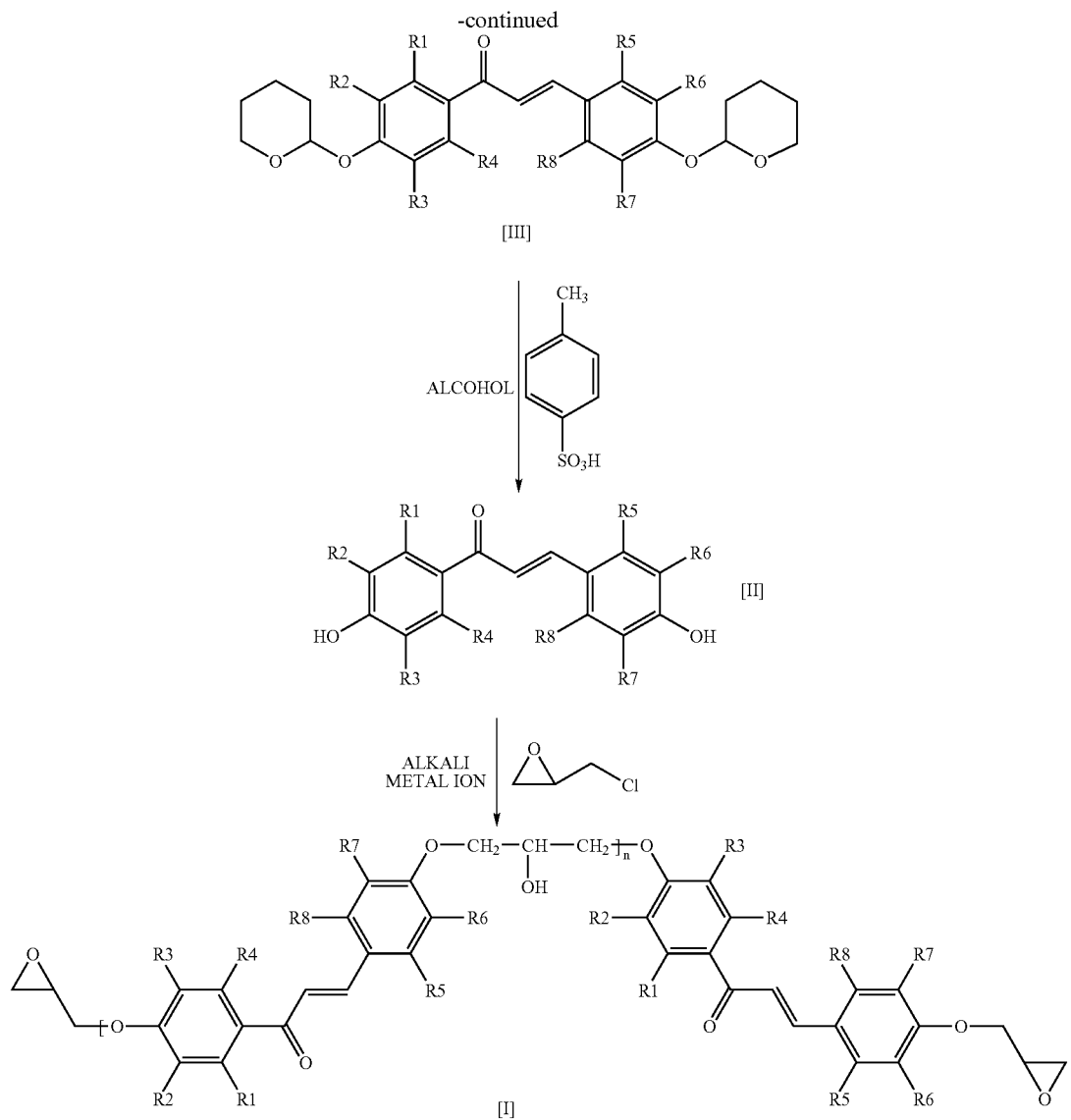
wherein n, $R_1$, $R_2$, $R_3$, $R_4$, $R_5$, $R_6$, $R_7$ and $R_8$ are as described above.
Photoresist Composition
A photoresist composition according to the present invention includes a curing agent, an organic solvent, and a compound represented by formula 1 as follows:
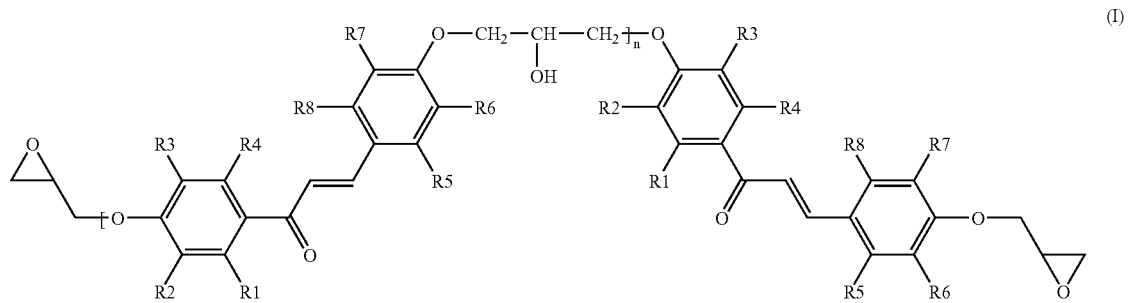

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, alkyl group, alkoxy group, halogen atom and nitro group. The photoresist composition remnant is reduced when using the photoresist composition according to the present invention.

The compound of formula (I) that has an epoxy group and a chalcone group is as described above, and is therefore not described in further detail here.

The photoresist composition includes about 5 to about 35 parts by weight of the compound of formula (I), about 0.01 to about 5 parts by weight of the curing agent and about 60 to about 90 parts by weight of the organic solvent.

When the photoresist composition includes more than 35 parts by weight of the compound of formula (I), mottle is regenerated in the liquid crystal display apparatus manufactured using the photoresist composition. When the photoresist composition includes less than 5 parts by weight of the compound, the adhering force of the photoresist composition is reduced, which is not preferable. Hence, the photoresist composition preferably includes about 5 to about 35 parts by weight of the compound of formula (I).

The curing agent enables a radiation curing process and a heat curing process to be performed at the same time or independently.

When the photoresist composition includes more than 5 parts by weight of the curing agent, the photoresist composition is prevented from fully curing which leads to a decrease in the adhesiveness of the photoresist composition. When the photoresist composition includes less than 0.1 parts by weight of the curing agent, curing speed decreases, which is not preferable. Thus, the photoresist composition preferably includes about 0.01 to about 5 parts by weight of the curing agent.

Examples of the curing agent include an acrylated monomer such as dipentaerithritol hexaacrylate, trimethylolpropane trimethacrylate, etc.

When the photoresist composition includes more than 90 parts by weight of the organic solvent, the adhering force of the photoresist composition is reduced, which is not preferable. When the photoresist composition includes less than 60 parts by weight of the organic solvent, mottle occurs in the liquid crystal display apparatus. Accordingly, the photoresist composition preferably includes about 60 to about 90 parts by weight of the organic solvent.

Any organic solvent that has proper viscosity and volatility may be used as the organic solvent. Examples of the organic solvent include propylene glycol monomethyl ether acetate, ethyl ethoxy acetate, cyclohexanone, etc.

When the photoresist composition including the compound of formula (I) is applied to a substrate and then exposed, a radical is generated from decomposition of the curing agent in the photoresist composition. The radical is cross-linked to the chalcone group in the compound of formula (I) to cure the photoresist composition.

The photoresist composition may further include an acrylate resin. The acrylate resin prevents lifting between the photoresist composition and a substrate where the photoresist composition is applied, thereby enhancing the adhesiveness of the photoresist composition. The acrylate resin is preferably used in substantially the same quantity as the compound according to the present invention.

The photoresist composition may further include a pigment. The pigment is dispersed in a solvent. The pigment is different from a dye in that the pigment is dissolved in a solvent.

Examples of a red pigment include color index (CI) Pigment RED 177, CI Pigment RED 254, etc. Examples of a green pigment include CI Pigment GREEN 36, etc. Examples of a yellow pigment include CI Pigment YELLOW 138, CI Pigment YELLOW 139, CI Pigment YELLOW 150, etc. Examples of a blue pigment include CI Pigment BLUE 15:6, etc. Examples of a violet pigment include CI Pigment VIOLET 23, etc.

The photoresist composition may further include a dispersant for dispersing the pigment in the photoresist composition. Generally, a mixture of the pigment and the dispersant is used. Examples of the mixture include products available from BYK-Chemie GmbH, Germany.

The photoresist composition may further include a photo-initiator. After absorption of light, the photo-initiator generates a lot of radicals. The radicals initiate a reaction. Examples of the photo-initiator include benzyl dimethyl ketal, diphenyl(2,4,6-trimethylbenzoyl)phosphine oxide, bis (trichloromethyl)-s-triazine derivatives, etc.

When the photoresist composition includes the pigment used for forming a color filter, the pigment adheres to the substrate having a black matrix by the radical that has been generated from the curing agent and cross-links to the chalcone group. Moreover, the surface of the photoresist composition is instantly cured in a photolithography process and the substrate is protected from impurities.

The photoresist composition is then cured by heat. The adhesiveness of the photoresist composition increases due to the epoxy group of the compound of formula (I). Hence, the photoresist composition firmly adheres to the substrate having patterns.

The chalcone group is connected to the main chain of the polymer compound of formula (I). The chalcone group may activate a cross-linking reaction and also serve as a binder. Thus, after a curing process, the surface of the photoresist composition becomes smooth and the photoresist composition remnant is not generated. However, when the chalcone group is attached to the side of the polymer compound, the chalcone group remains in the form of a thread after the curing process. Hence, the surface of the photoresist composition becomes rough and the photoresist composition remnant may be generated.

The chalcone group as a polymer binder enhances an adhesive force between the substrate having black matrix patterns and the photoresist pattern during application of the photoresist composition. The chalcone group also maintains a uniform thickness of the photoresist composition. When manufacturing the color filter, preferably, the compound having the chalcone group is uniformly dispersed in the photoresist composition together with pigments and dispersants for the pigments. To be uniformly dispersed, the photoresist composition has different amounts of the compound having the chalcone group depending on the pigments employed.

When the compound having the chalcone group is cured, a photoresist layer having a higher degree of cross-linking than that of a photoresist layer using a conventional acrylate resin is obtained. Thus, the curing process is completely carried out and there is no remnant. Therefore, the interaction between the photoresist layer and other materials is reduced. Because there is little remnant in the photoresist layer, the photoresist pattern is maintained in a good state in the successive process of forming a photoresist multilayer pattern. Consequently, the color filter using a compound having an epoxy group and a chalcone group according to the present invention has high color reproductivity and high brightness.

The photoresist composition may be used, for example, in a liquid crystal display apparatus, e.g., organic electroluminescent apparatus or inorganic electro-luminescent apparatus.

The photoresist composition according to the present invention is prepared by dissolving the compound of formula (I) and the curing agent in an organic solvent and then dispersing the compound and the curing agent in the organic solvent.

The compound of formula (I) may be used in the manufacture of a photoresist pattern used in a color filter. Hereinafter, the photoresist that includes a pigment and used in a color filter is referred to as a 'color resist'.

A color resist composition including the compound of formula (I), a curing agent and an organic solvent is applied to an underlying layer on a substrate to form a color resist layer. The color resist layer is then exposed and developed to form a color resist pattern.

The process of forming the color resist pattern is performed by a conventional method of forming a photoresist pattern except that the process of stripping the photoresist composition is not performed. The underlying layer may be an insulation layer having a black matrix or an insulation layer having another color resist pattern.

Figure 1B:
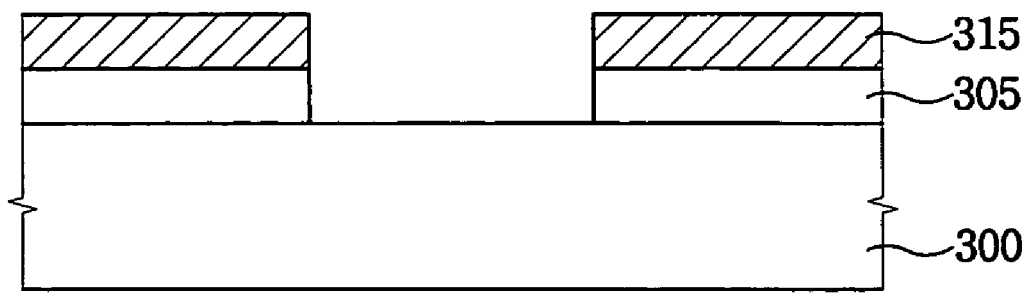

The process of forming the color resist pattern is depicted in FIGS. 1A and 1B.

FIGS. 1A and 1B are cross-sectional views illustrating a process of forming the color resist pattern using a compound according to the exemplary embodiments of the present invention.

Referring to FIG. 1A, a black matrix 305 is formed on a substrate 300. The substrate 300 includes glass, and the black matrix 305 includes chromium oxide. The black matrix 305 may include a single layer or a double layer of chromium oxide.

A color resist composition includes a compound according to the present invention, a curing agent and an organic solvent. The color resist composition is applied to the black matrix 305 to form a color resist layer 310. The color resist layer 310 is baked at the temperature of about 80 to about 130° C. to evaporate the organic solvent. This process is referred to as a soft bake process. While the organic solvent is evaporated, the compound that has the epoxy group and the chalcone group in the color resist composition does not thermally decompose. Thus, the compound can be cured by radiation and heat. After the organic solvent is evaporated, the color resist layer 310 has a thickness of about less than 2 μm.

A mask 350 having patterns is disposed over the color resist layer 310. An ultraviolet (UV) ray 370 is irradiated onto the color resist layer 310 through the mask 350. A portion of the color resist layer 310 is exposed to the ultraviolet ray 370 upon the pattern of the mask 350. The exposed portion of the color resist layer 310a undergoes a photo reaction to be soluble in a subsequent developing process.

The substrate 300 having the exposed color resist layer 310a is dipped into an alkaline developing solution. Then, the exposed color resist layer 310a is dissolved in the developing solution. Examples of the alkaline developing solution include hydroxides of alkali metals, ammonium hydroxides, tetramethyl ammonium hydroxides, etc.

The substrate 300 is then taken out of the developing solution and heated to a temperature of about 90 to about 140° C. to enhance adhesion and chemical resistance of the color resist layer 310. This process is referred to as a hard bake process. The hard bake process is performed under a softening temperature of the color resist layer 310. If the hard bake process is carried out at or over the softening temperature of the color resist layer 310, the color resist layer 310 may collapse. Through this hard bake process, a color resist pattern 315 is formed.

When forming color filters, after forming the color resist pattern 315, another color resist composition may be applied to the substrate, exposed and then developed to form another color resist pattern on the substrate and a color resist multilayer pattern on the black matrix. This procedure is repeated to form an overall color resist pattern.

Hereinafter, the present invention is described in detail with reference to the following examples. The examples are given solely for the purpose of illustration and are not to be construed as limitations of the present invention, as many variations thereof are possible without departing from the spirit and scope of the invention.

EXAMPLE 1

Preparation of a Compound Having the Epoxy Group and the Chalcone Group (i) Synthesis of 4-(2-tetrahydro-2H-pyranoxy)acetophenone and 4-(2-tetrahydro-2H-pyranoxy)benzaldehyde 5 g (0.0367 mol) of 4-hydroxy acetophenone was dissolved in 150 ml of chloroform. 3.09 g (0.0367 mol) of 3,4-dihydro-2H-pyran and 930 mg (0.0037 mol) of pyridium paratoluene sulfonic ester as a catalyst were added and then the reaction mixture was stirred at room temperature for about 8 hours. The reaction mixture was extracted with water and chloroform and precipitated using hexane at a temperature of 0 to about 5° C. and then dried. Approximately 6.48 g (0.0294 mol) of 4-(2-tetrahydro-2H-pyranoxy)acetophenone was obtained. The yield of the reaction was about 80%.

5 g (0.0409 mol) of 4-hydroxy benzaldehyde was dissolved in 150 ml of chloroform. 3.44 g (0.0409 mol) of 3,4-dihydro-2H-pyran and 1.03 g (0.0041 mol) pyridium paratoluene sulfonic ester as a catalyst were added while stirring. The reaction mixture was then stirred at room temperature for about 8 hours. The reaction mixture was extracted using water and chloroform and precipitated using hexane at a temperature of 0 to about 5° C. and then dried. Approximately 7.17 g (0.0348 mol) of 4-(2-tetrahydro-2H-pyranoxy)benzaldehyde was obtained. The yield of the reaction was about 85%.

(ii) Synthesis of bis[4,4'-(2,2'-tetrahydro-2H-pyranoxy)] chalcone 10 g (0.048 mol) of 4-(2-tetrahydro-2H-pyranoxy)acetophenone and 10.57 g (0.048 mol) of 4-(2-tetrahydro-2H-pyranoxy)benzaldehyde were dissolved in 200 ml of ethanol. An aqueous sodium hydroxide solution was slowly added to the reaction mixture at room temperature. A thin layer chromatography was conducted every hour to check the progress of the reaction. After 10 hours, the reaction was terminated. The reaction compound was extracted with chloroform as an organic solvent and then precipitated.

Approximately 14.71 g (0.036 mol) bis[4,4'-(2,2'-tetrahydro-2H-pyranoxy)]chalcone was obtained. The yield of the reaction was about 75%.

(iii) Synthesis of bis(4,4'-hydroxy)chalcone 10 g (0.024 mol) of bis[4,4'-(2,2'-tetrahydro-2H-pyranoxy)]chalcone was dissolved in 200 ml of ethanol at the temperature of about 50 to about 60° C. while stirring for 30 minutes. Then, 603 mg (0.0024 mol) of paratoluene sulfonic acid was added, and the reaction was maintained for about 4 hours. The product was precipitated using tetrahydrofuran and hexane. Approximately 5.19 g (0.0216 mol) of bis(4,4'-hydroxy)chalcone was obtained. The yield of the reaction was about 90%.

(iv) Synthesis of a Compound Having an Epoxy Group and a Chalcone Group 5 g (0.0208 mol) of bis(4,4'-hydroxy)chalcone and 385 g (4.16 mol) of epichlorohydrin were mixed at about 40° C. An aqueous sodium hydroxide solution was slowly added to the reaction mixture. The reaction mixture was stirred for about 12 hours at about 40° C., extracted with water and toluene and then dried to obtain approximately 11.4 g of an aqueous compound having an epoxy group and a chalcone group. The compound had a weight average molecular weight of about 900.

(v) Determination of the Compound $^1$H-NMR (300 MHz, CDCl$_3$) spectrum of the compound was obtained.

Figure 2:
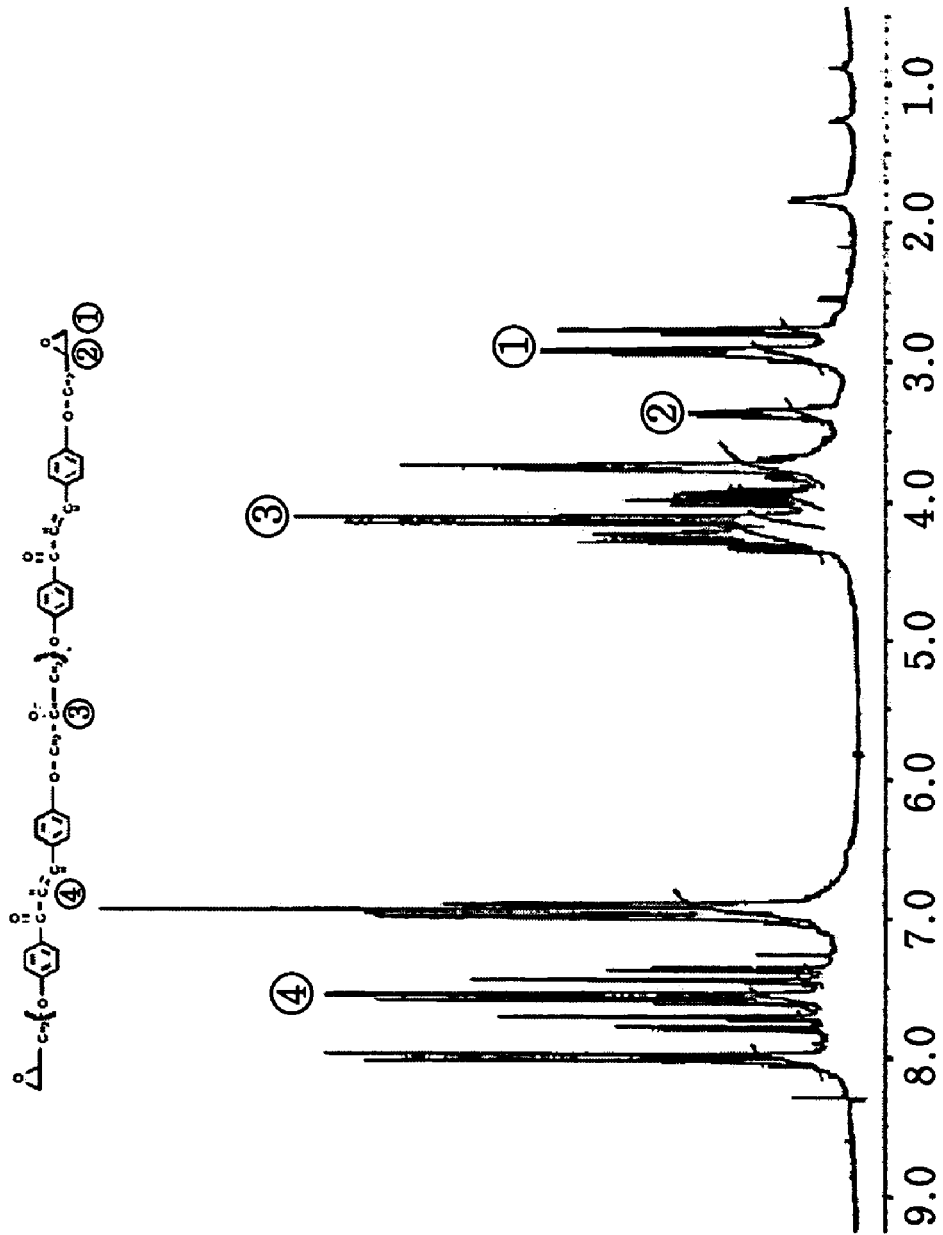
FIG. 2 is a NMR spectrum of the compound obtained in Example 1 having an epoxy group and a chalcone group.

FIG. 2 is an NMR spectrum of the compound obtained in Example 1 having the epoxy group and the chalcone group.

Hydrogen atoms of the epoxy group(①and②), hydrogen atom from epichlorohydrin(③), hydrogen atom of the enone group(④) are shown in the $^1$H-NMR spectrum of FIG. 2. It is clear that the compound obtained in Example 1 has an epoxy group and a chalcone group.

The infrared spectra of the compound were obtained. FIG. 3A represents infrared spectra of the compound obtained in Example 1 with respect to time. FIG. 3B represents enlarged infrared spectra of FIG. 3A having a wave number of 1500 to 1700 cm. In infrared spectra, the light source is an ultraviolet ray having a wavelength of about 365 nm, and the intensity of the light is 12.73 mV/cm$^2$.

Referring to FIGS. 3A and 3B, an absorption band is observed near the wave number of 914 cm$^{-1}$ that corresponds to an epoxy ring. Another absorption band near the wave number of 1600 cm$^{-1}$ corresponds to a carbon-carbon double bond in the chalcone group.

Meanwhile, when the ultraviolet ray is irradiated onto the chalcone group, the carbon-carbon double bond in the chalcone group reacts with another carbon-carbon double bond in another chalcone group to form a carbon-carbon single bond. The carbon-carbon double bond disappears with time. Thus, by analyzing the infrared spectrum representing the carbon-carbon double bond, the photochemical reactivity of the compound may be confirmed.

In FIGS. 3A and 3B, spectrum 'A' corresponds to the infrared spectrum right after the radiation of the ultraviolet ray. Spectrum 'B' corresponds to the infrared spectrum 10 minutes after the radiation. Spectrum 'C' corresponds to the infrared spectrum 30 minutes after the radiation, and spectrum 'D' corresponds to the infrared spectrum 60 minutes after the radiation. Referring to FIG. 3B, it can be noted that the peak near the wave number of 1600 cm$^{-1}$ represents that the carbon-carbon double bond has been reduced 60 minutes after the radiation. Thus, it is clear the chalcone group in the compound obtained in Example 1 reacts with light.

It can also be noted from the spectra that the compound obtained in Example 1 has both a chalcone group having a radiation curing property and an epoxy group having a heat curing property.

EXAMPLE 2

Synthesis of Photoresist Composition 63.5 g of the compound obtained in Example 1, 63.5 g of acrylate resin, 2 g of dipentaerithritol hexaacrylate as a curing agent, 1 g of diphenyl(2,4,6-trimethylbenzoyl)phosphine oxide as a photo-initiator and 225 g of a mixture of a green pigment and a dispersant for the pigment were added to 145 g of propylene glycol monomethyl ether acetate. The reaction mixture was stirred at room temperature for about 3 hours and then filtered using a filter having a pore size of 2.5 μm to obtain about 410 g of a green color resist composition.

Comparative Example 1

Synthesis of a Conventional Photoresist Composition 127 g of acrylate resin, 2 g of dipentaerithritol hexaacrylate as a curing agent, 1 g of diphenyl(2,4,6-trimethylbenzoyl)phosphine oxide as a photo-initiator and 225 g of a mixture of a green pigment and a dispersant for the pigment were added to 145 g of propylene glycol monomethyl ether acetate. The reaction mixture was stirred at room temperature for about 3 hours to obtain about 390 g of a green color resist composition.

Experiment 1: Color Reproductivity and Brightness

Red and blue color resist compositions were synthesized to be used with the green color resist composition obtained in Example 2. Color reproductivity and brightness of the photoresist composition according to an exemplary embodiment of the present invention were tested.

(i) Synthesis of Red Color Resist Composition 100 g of acrylate resin, 1 g of dipentaerithritol hexaacrylate as a curing agent, 1 g of diphenyl(2,4,6-trimethylbenzoyl)phosphine oxide as a photo-initiator and 200 g of a mixture of a red pigment and a dispersant for the pigment were added to 180 g of propylene glycol monomethyl ether acetate. Then, the reaction mixture was stirred at room temperature for about 3 hours. The reaction mixture was filtered using a filter having a pore size of 2.5 μm to obtain about 388 g of a red color resist composition.

(ii) Synthesis of Blue Color Resist Composition 112.5 g of acrylate resin, 1.5 g of dipentaerithritol hexaacrylate as a curing agent, 1 g of diphenyl(2,4,6-trimethylbenzoyl)phosphine oxide as a photo-initiator and 210 g of a mixture of a blue pigment and a dispersant for the pigment were added to 175 g of propylene glycol monomethyl ether acetate. Then, the reaction mixture was stirred at room temperature for about 3 hours. The reaction mixture was filtered using a filter having a pore size of 2.5 μm to obtain about 395 g of a blue color resist composition.

The red color resist composition obtained above, green color resist composition obtained in Example 2 and blue color resist composition obtained above were sequentially applied to a silicon substrate, and the substrate was baked at about 100° C. by a soft baking process. An ultraviolet ray was irradiated onto the substrate through a mask having patterns. The exposed substrate was dipped into an alkaline developing solution, and then the substrate was heat treated to obtain a color resist pattern on the substrate. The color resist pattern was formed of a monolayer or multilayer. The color reproductivity and brightness of the color filter using the color resist pattern was determined. The properties including the brightness are shown in Table 1 below.

TABLE 1

Color coordinate (x, y) and brightness (Y)

| Color resist pattern | x | y | Y |
|---|---|---|---|
| red color resist monolayer pattern | 0.6464 | 0.3420 | 21.90 |
| green color resist monolayer pattern | 0.3012 | 0.5720 | 61.81 |
| blue color resist monolayer pattern | 0.1380 | 0.1280 | 16.37 |
| red color resist multilayer pattern | 0.6397 | 0.3426 | 23.03 |
| green color resist multilayer pattern | 0.3006 | 0.5699 | 61.90 |
| blue color resist multilayer pattern | 0.1383 | 0.1302 | 16.63 |

As shown in Table 1, the x color coordinate of the green color resist monolayer pattern is 0.3012 and the x color coordinate of the green multilayer pattern is 0.3006. The difference between them is insignificant. Thus, it can be noted that the color reproductivity of the green color resist multilayer pattern is excellent.

The y color coordinate of the blue color resist monolayer pattern is 0.1280, and the y color coordinate of blue color resist multilayer pattern is 0.1302. The difference between them is insignificant. Thus, it can be noted that the color reproductivity of the blue color resist multilayer pattern is excellent.

Y represents brightness of a color filter. As shown in Table 1, the Y values in the multilayers are greater than the Y values than in the monolayers, thereby showing the brightness of the color resist in the multilayer patterns has not been reduced.

Comparative Experiment 1

The procedure of Experiment 1 was repeated except that a conventional green color resist composition obtained in Comparative Example 1 was used to determine the color reproductivity and brightness. The color characteristics of monolayers and multilayers are shown in FIG. 4. The properties including brightness are shown in Table 2.

FIG. 4 is a graph illustrating color characteristics of monolayer and multilayer patterns using the conventional photoresist composition of Comparative Example 1.

As shown in FIG. 4, color coordinates of the green and blue color resist multilayer patterns are moved from those of monolayer patterns. This indicates that during application of another color resist composition on a color resist monolayer pattern, the color resist composition that is supposed to be removed remains causing movement of the color coordinates. Thus, the remnant ascribes to the incomplete curing of the acrylate resin.

TABLE 2

Color coordinate (x, y) and brightness (Y)

| Color resist pattern | x | y | Y |
|---|---|---|---|
| red color resist monolayer pattern | 0.6357 | 0.3424 | 23.73 |
| green color resist monolayer pattern | 0.3104 | 0.5562 | 66.75 |
| blue color resist monolayer pattern | 0.1437 | 0.1459 | 20.34 |
| red color resist multilayer pattern | 0.6345 | 0.3423 | 23.54 |
| green color resist multilayer pattern | 0.2862 | 0.5677 | 57.45 |
| blue color resist multilayer pattern | 0.1394 | 0.1298 | 16.66 |

As shown in Table 2, the x color coordinate of a green color resist monolayer pattern is 0.3104 and the x color coordinate of a green color resist multilayer pattern is 0.2862. The difference between the x color coordinates above is greater than that of Experiment 1. Hence, the color reproductivity of the green color resist multilayer pattern is not satisfactory.

The y color coordinate of the blue color resist monolayer pattern is 0.1459, and the y color coordinate of the blue color resist multilayer pattern is 0.1298. The difference between the y color coordinates above is greater than that of Experiment 1. Thus, color reproductivity of the blue color multilayer pattern is not satisfactory.

When comparing the color coordinates of each of the red, green and blue color resist monolayer patterns with those of multilayer patterns, color coordinates of green and blue color resist multilayer patterns are significantly moved representing a reduction of color reproductivity.

Y, which represents brightness, of the multilayer patterns is significantly reduced as compared to the Y of the monolayer patterns. Thus, the color resist multilayer pattern using the conventional color resist composition has reduced brightness.

Experiment 2: Shape and Surface Roughness of Pattern

A color resist pattern was formed using the color resist composition obtained in Example 1. The shape and surface roughness of the color resist pattern was observed by a scanning electron microscope (SEM).

Figure 5:
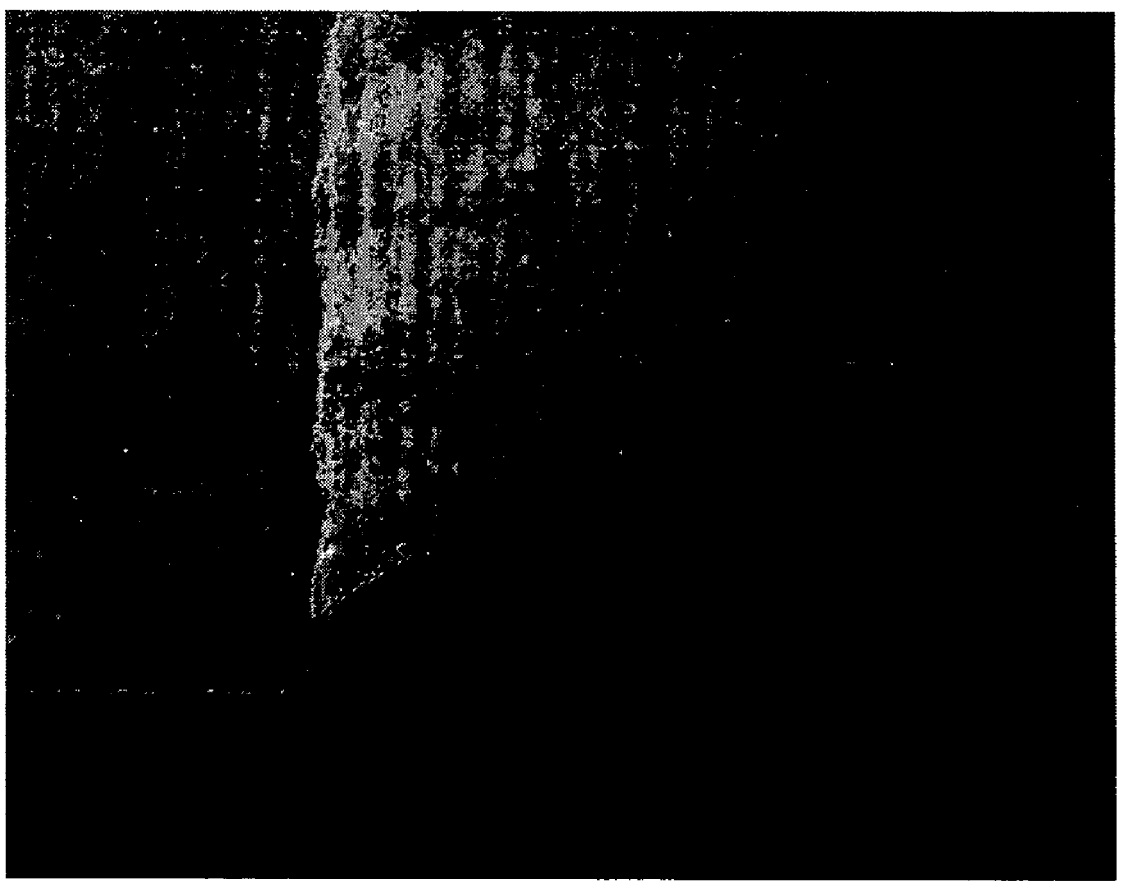
FIG. 5 is an electron microscope photograph illustrating the shape of the color resist pattern obtained in Experiment 2.
Figure 6:
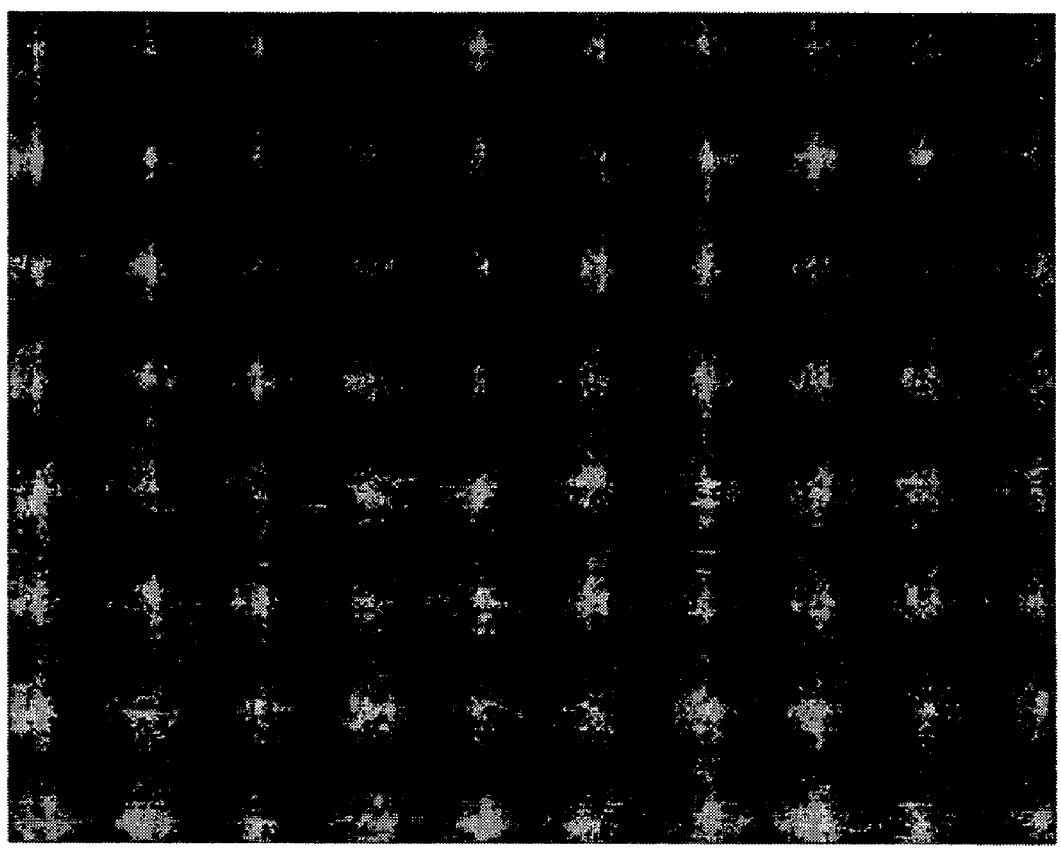
FIG. 6 is an electron microscope photograph illustrating the surface condition of a portion of the color resist pattern obtained in Experiment 2.

FIG. 5 is an electron microscope photograph illustrating the shape of the color resist pattern obtained in Experiment 2. FIG. 6 is an electron microscope photograph illustrating the surface condition of a portion of the color resist pattern obtained in Experiment 2.

Referring to FIG. 5, a color resist monolayer pattern is adjacent to a color resist multilayer pattern. The portion where the color resist monolayer pattern is adjacent to the color resist multilayer pattern is smooth. Moreover, each of the color resist monolayer and multilayer patterns is not collapsed or cracked.

Referring to FIG. 6, the surface of the color resist pattern is smooth. The surface roughness of the color resist pattern is 52 Å.

The color resist pattern using a compound according to the present invention shows excellent color reproductivity and brightness after forming a color resist multilayer pattern.

Comparative Experiment 2

A color resist pattern was formed using a conventional color resist composition including the acrylate resin. The shape and surface roughness of the color resist pattern was observed by a scanning electron microscope (SEM).

Figure 7:
FIG. 7 is an electron microscope photograph illustrating the shape of the color resist pattern obtained in Comparative Experiment 2.
Figure 8:
FIG. 8 is an electron microscope photograph illustrating the surface condition of a portion of the color resist pattern obtained in Comparative Experiment 2.

FIG. 7 is an electron microscope photograph illustrating the shape of the color resist pattern obtained in Comparative Experiment 2. FIG. 8 is an electron microscope photograph illustrating the surface condition of a portion of the color resist pattern obtained in Comparative Experiment 2.

Referring to FIG. 7, a color resist monolayer pattern is adjacent to a color resist multilayer pattern. The portion where the color resist monolayer pattern is adjacent to the color resist multilayer pattern is rough. Moreover, the color resist multilayer pattern is partially collapsed.

Referring to FIG. 8, the surface of the color resist pattern is rough. The surface roughness of the color resist pattern is 210 Å, which is greater than that of Experiment 2.

Further, the color resist pattern using the acrylate resin has reduced color reproducibility and brightness.

A photoresist composition including a compound according to the present invention has the following advantages.

The photoresist composition including a compound according to the present invention has substantially no remnant. Thus, the photoresist composition may be used in a large display apparatus or a fine pitch display apparatus.

Further, the photoresist composition including a compound of the present invention substantially prevents the formation of remnant in a color resist pattern, changes of color coordinates of a color resist pattern and the reduction of brightness during the formation of a multilayer color pattern, thereby forming a color filter having improved color reproductivity and brightness.

Having described the exemplary embodiments of the present invention and its advantages, it is noted that various changes, substitutions and alterations can be made herein without departing from the spirit and scope of the present invention as defined by appended claims.

What is claimed is:

1. A resist composition comprising:
   (a) a compound comprising an epoxy group and a chalcone group represented by the following formula:

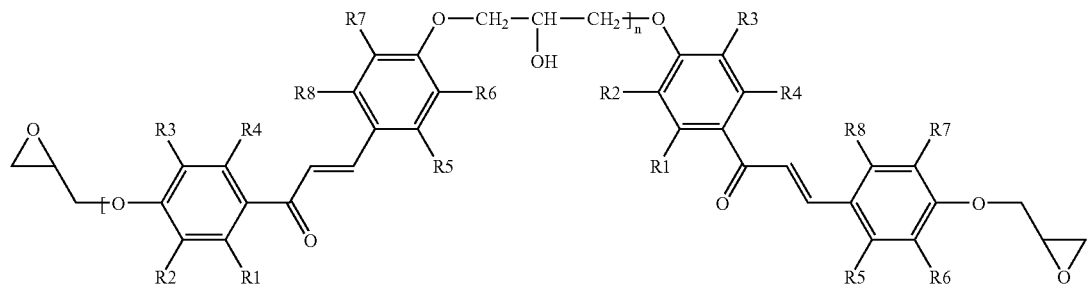

wherein n is an integer from 1 to 10,000 and each of $R_1$, $R_2$, $R_3$, $R_4$, $R_5$, $R_6$, $R_7$ and $R_8$ is selected from a group consisting of a hydrogen atom, an alkyl group, an alkoxy group, a halogen atom and a nitro group;

(b) an acrylate resin;
   (c) a curing agent; and
   (d) an organic solvent.

2. The resist composition of claim 1, wherein the resist composition includes about 5 to about 35 parts by weight of the compound, about 0.01 to about 5 parts by weight of the curing agent, and about 60 to about 90 by weight of the organic solvent.

3. The resist composition of claim 1, wherein the organic solvent is propylene glycol monomethyl ether acetate, ethyl ethoxy acetate, or cyclohexanone.

4. The resist composition of claim 1, wherein the resist composition includes about 5 to about 35 parts by weight of a combination of the acrylate resin and the compound, about 0.01 to about 5 parts by weight of the curing agent, and about 60 to about 90 by weight of the organic solvent.

5. The resist composition of claim 1, further comprising a pigment, wherein the pigment is dissolved in a solvent.

6. The resist composition of claim 5, further comprising a dispersant for dispersing the pigment in the photoresist composition.

7. The resist composition of claim 1, further comprising a photo-initiator.

8. The resist composition of claim 7, wherein the photo-initiator is benzl dimethyl ketal, diphenyl(2,4,6-trimethylbenzoyl)phosphine oxide, or bis(trichloromethyl)-s-triazine derivative.

9. The resist composition according to claim 1, wherein the compound has a weight average molecular weight of about 800 to about 20,000.

10. The resist composition according to claim 5, wherein the pigment is a red, blue, green, yellow, or violel pigment.

11. The resist composition according to claim 1, wherein the curing agent is a dipentaerithritol hexaacrylate or a trimethylolpropane trimethacrylate.

* * * * *